US008952173B2

United States Patent
Silva Guisasola et al.

(10) Patent No.: US 8,952,173 B2
(45) Date of Patent: Feb. 10, 2015

(54) METHOD FOR THE RESOLUTION OF 2-AMINO-6-PROPYLAMINO-4,5,6,7-TETRAHYDROBENZOTHIAZOL AND INTERMEDIATE COMPOUNDS

(75) Inventors: Luis Octavio Silva Guisasola, Boecillo-Valladolid (ES); Jorge Martin Juarez, Boecillo-Valladolid (ES)

(73) Assignee: Crystal Pharma, S.A.U., Boecillo, Valladolid (ES)

( * ) Notice: Subject to any disclaimer, the term of this patent is extended or adjusted under 35 U.S.C. 154(b) by 1807 days.

(21) Appl. No.: 11/913,842

(22) PCT Filed: May 9, 2006

(86) PCT No.: PCT/ES2006/000226
§ 371 (c)(1), (2), (4) Date: Apr. 3, 2008

(87) PCT Pub. No.: WO2006/120268
PCT Pub. Date: Nov. 16, 2006

(65) Prior Publication Data
US 2008/0194832 A1 Aug. 14, 2008

(30) Foreign Application Priority Data

May 9, 2005 (ES) .................................. 200501103

(51) Int. Cl.
*C07D 277/82* (2006.01)

(52) U.S. Cl.
CPC .................................. *C07D 277/82* (2013.01)
USPC .......................................................... 548/164

(58) Field of Classification Search
USPC .......................................................... 548/164
See application file for complete search history.

(56) References Cited

U.S. PATENT DOCUMENTS

| | | | |
|---|---|---|---|
| 4,731,374 A | 3/1988 | Griss et al. | |
| 4,843,086 A | 6/1989 | Griss et al. | |
| 4,886,812 A | 12/1989 | Griss et al. | |
| 4,988,699 A | 1/1991 | Caprathe et al. | 514/253.1 |
| 6,727,367 B2 | 4/2004 | Pospisilik | |
| 6,770,761 B2 | 8/2004 | Pospisilik et al. | |
| 2003/0092773 A1* | 5/2003 | Evans | 514/650 |

FOREIGN PATENT DOCUMENTS

| | | |
|---|---|---|
| EP | 0207696 A1 | 1/1987 |
| ES | 550235 | 12/1985 |
| ES | 556873 | 7/1986 |
| ES | 556874 | 7/1986 |
| ES | 556875 | 12/1986 |
| ES | 8702787 A1 | 4/1987 |
| ES | 2187249 B1 | 9/2004 |
| ES | 2245604 A1 | 1/2006 |
| GB | 2382074 A * | 5/2003 |
| WO | WO 02/22591 | 3/2002 |
| WO | 2006/117614 A1 | 11/2006 |

OTHER PUBLICATIONS

Schneider, C.S., et al., "Dopamine Autoreceptor Agonists: Resolution and Pharmacological Activity of 2,6-Diaminotetrahydrobenzothiazole and an Aminothiazole Analogue of Apomorphine," J. Med. Chem. 1987, pp. 494-498, vol. 30.
PCT Search Report from PCT/ES2006/000226 dated Sep. 22, 2006 (untranslated).
PCT Written Opinion from PCT/ES2006/000226 dated Sep. 22, 2006, and its English translation.
PCT International Preliminary Report on Patentability Chapter I from PCT/ES2006/000226 dated Mar. 26, 2008, and its English translation.
B. Jancic et al., "Chromatographic Determination of Dissociation Constants of Primipexole and its Impurities", Chromatographia 2007, 65, ,May (No. 9/10) p. 633 (http://link.springer.com/article/10.1365/s10337-007-0199-5—p. 1, last accessed Sep. 12, 2014.).
Jaydeep S. Patel et al., "Determination of dissociation constant of pramipexole dihydrochloride by UV-visible spectrophotometry" (abstract only, available at scientificpca.org/paper/2012/08/28/201208281532070A.docx, last accessed Sep. 12, 2014.).
Tomasz Giller, "Iontophoretic Delivery of Selected Antiparkinsonian Agents in Vitro" (PhD thesis, University of Bath, U.K., Mar. 2009, available at http://opus.bath.ac.uk/17245/1/Giller-T-PhD-2009.pdf , last accessed Sep. 12, 2014.).
Hitesh B. Patel, "HPLC Method Development and Quantitation for Pharmaceutical Compounds", (PhD thesis, Saurashtra Unversity, India, 2008, available at http://etheses.saurashtrauniversity.edu/439/1/patel_hb_thesis_chemistry.pdf, last accessed Sep. 12, 2014.).

\* cited by examiner

*Primary Examiner* — Laura L. Stockton
(74) *Attorney, Agent, or Firm* — Ladas & Parry, LLP

(57) ABSTRACT

The invention relates to a novel method for the resolution of the racemic mixture of compound (R,S)-2-amino-6-propylamino-4,5,6,7-tetrahydrobenzothiazole, or the enrichment of same with in one of its enantiomers, and to intermediate compounds which can be used to perform said method.

9 Claims, No Drawings

METHOD FOR THE RESOLUTION OF 2-AMINO-6-PROPYLAMINO-4,5,6,7-TETRAHYDROBENZOTHIAZOL AND INTERMEDIATE COMPOUNDS

CROSS REFERENCES TO RELATED APPLICATIONS

This application is the national stage entry of PCT/ES06/00226.

FIELD OF THE INVENTION

The present invention refers to a new process for the resolution into, or enrichment in one of its enantiomers, of the racemic mixture of the compound (R,S)-2-amino-6-propylamino-4,5,6,7-tetrahydrobenzothiazole, and to intermediate compounds useful for carrying out said process.

BACKGROUND OF THE INVENTION

The 4,5,6,7-tetrahydrobenzothiazole compounds of general formula (A):

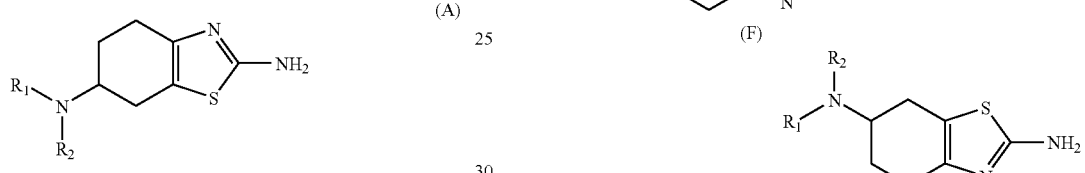

also referred to as 2-amino-6-($R_1$,$R_2$)amino-4,5,6,7-tetrahydrobenzothiazoles, wherein $R_1$ is hydrogen, alkyl or aralkyl and $R_2$ is hydrogen, are known as useful pharmacological agents.

Among these compounds, the S-enantiomer of 2-amino-6-propylamino-4,5,6,7-tetrahydrobenzothiazole, known as pramipexole, which is a commercial product with dopamine $D_2$ agonist activity, must be highlighted. This product is marketed in dihydrochloride form for the treatment of Parkinson's disease, schizophrenia or hypertension, under different trademarks, such as Mirapexin® for example.

2-amino-6-propylamino-4,5,6,7-tetrahydrobenzothiazole is described for the first time in EP 186 087, in addition to other related compounds and their use. Within the family of patents to which it belongs there are other documents, such as U.S. Pat. No. 4,731,374 and its divisional patents U.S. Pat. No. 4,843,086 and U.S. Pat. No. 4,886,812; ES 550235 and its divisional patents ES 556873, ES 556874 and ES 556875, which also describe analogous compounds and processes of obtaining them.

The compounds of general formula (A) have an asymmetrical carbon atom and can exist either as pure enantiomeric forms or as mixtures thereof. However the pharmacological activity of said compounds is much greater in one of its enantiomeric forms, as occurs for example with pramipexole, which is marketed as the substantially pure S(−) isomer given that the dopaminergic activity of said isomer is two times greater than that of the R(+) isomer. Though the previously mentioned state of the art claims the possible enantiomers, it only allows the preparation of the racemate as it is understood from the described examples.

The first bibliographic reference in which a process for obtaining the different enantiomers of 2-amino-6-propylamino-4,5,6,7-tetrahydrobenzothiazole is described is a publication of Schneider and Mierau in the *J. Med. Chem.*, 1987, 30, 494. In said publication, pramipexole is not directly resolved from the racemic mixture but from a precursor of it, specifically compound (A) wherein $R_1=R_2=H$, which is reacted with L(+)-tartaric acid acting as a resolving agent.

After said resolution, the optically active pramipexole is prepared by means of a two-step propylation of the pure enantiomer of the diaminated precursor, comprising reaction with propionic anhydride followed by reduction of the propionylated intermediate. The rotatory power value described in this publication for pramipexole dihydrochloride is $\alpha_D=-67.2°$ (c=1 $CH_3OH$).

In turn, ES 2187249 describes obtaining the compound of formula (A) enriched in the desired enantiomer by means of a synthetic route such as the one described below:

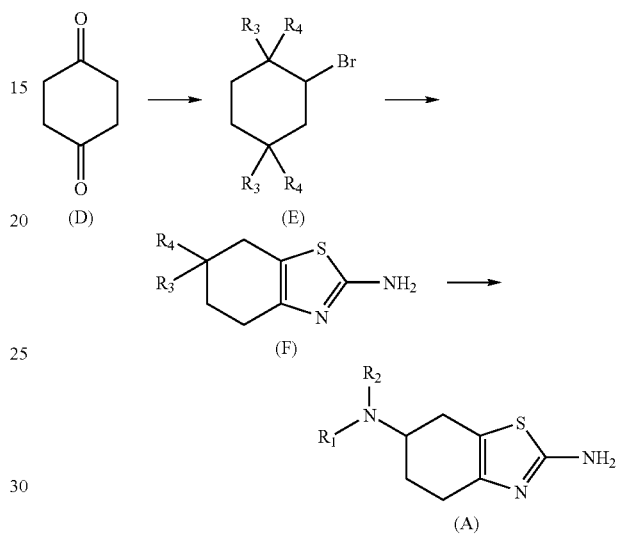

This process comprises the selective monobromination of cyclohexanedione (D) in an alcoholic solvent to give the compound of formula (E) wherein $R_3$ and $R_4$ are the same or each one represents an 1-4 carbon atom alkoxy group, or together form a $C_2$-$C_5$ alkylenedioxy group or an oxo-group; a condensation with a thiourea gives a compound of formula (F) and finally, a reaction of said compound (F) with a suitable amine under reductive amination conditions. This method allows producing pramipexole substantially enriched in the desired S(−) enantiomer by using a chiral catalyst for the reductive amination to propylamine or by using a chiral amine convertible to propylamine as a reagent in reductive amination.

Example 6 of said patent also describes a process for the resolution of racemic pramipexole base using L(+)-tartaric acid to obtain pramipexole tartrate and subsequently pramipexole dihydrochloride. The obtained results however reflect a rotatory power value of only $\alpha_D=-48.8°$ (c=1, MeOH), which does not correspond to an optically pure product in view of the mentioned prior art, but rather to a mixture of (S)-enantiomer-enriched enantiomers.

Patent application WO 02/22591 describes a process for the resolution of pramipexole, consisting of, given the dibasic character of pramipexole, forming an intermediate mono-salt of general formula:

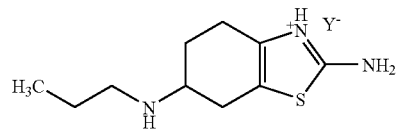

wherein Y is the monovalent anion derivative of an acid selected from hydrochloric, hydrobromic, hydriodic, nitric, benzoic, acetic, methanesulfonic, ethanesulfonic, trifluoromethanesulfonic, benzenesulfonic and paratoluenesulfonic acid, and then forming a di-salt of general formula:

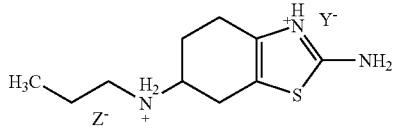

wherein Y is as hereinbefore defined and Z is the anion derivative of an optically active acid selected from L-tartaric, di-p-toluyl-D-tartaric and dibenzoyl-D-tartaric acid. The "mixed" diastereoisomeric salts are split by crystallization in the described process. The rotatory power values obtained in this publication for pramipexole dihydrochloride are $\alpha_D = -66.5°$, C=1, $CH_3OH$ (at the very best, see Example 1-d).

In this case, even though a product with a greater enantiomeric purity in the pramipexole (S) isomer is obtained, it is necessary to carry out several steps which complicate and prolong the process, such as the initial formation of a mono-salt of the product and its subsequent isolation then followed by a second step comprising the addition of an optically active acid, and finally one or more additional steps are necessary for obtaining by diastereoselective recrystallization one of the diastereomeric salts which provides the suitable isomer by subsequent release.

On the other hand, though the obtained rotatory power values are more satisfactory than in the prior art, they do not correspond to a product complying with the high optical purity requirements necessary for products with pharmacological activity, such as pramipexole.

Therefore despite the existence of processes allowing the resolution of racemic pramipexole by fractionated crystallization using classic resolving agents such as chiral acids, such as tartaric, di-p-toluyl-D-tartaric, mandelic acid, etc. . . . , in organic solvents, these lead to compounds with low optical purity and little reproducibility. This has caused there to be a serious need to develop alternative processes which allow obtaining enantiomers of a high optical purity.

BRIEF DESCRIPTION OF THE INVENTION

An object of the present invention consists of a process for the resolution into one of the enantiomers of the racemate of the compound of formula (I)

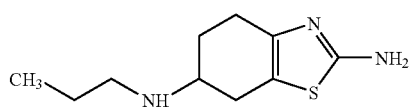

or for the enrichment of a mixture with any enantiomeric excess of said compound of formula (I), comprising the following steps:
  a) reacting said racemate, or said mixture with any enantiomeric excess of the compound of formula (I), with any of the enantiomers of a chiral acid of formula (IV):

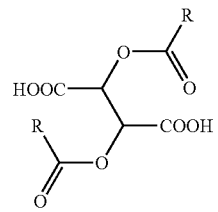

wherein R is monosubstituted phenyl or alkylphenyl,
  in an organic solvent or in a mixture of said organic solvent and water; and
  b) obtaining, by means of crystallization or fractionated crystallization of the reaction mixture of step a), an optically pure diastereoisomeric mono-salt or a mono-salt enriched in any of its two possible diastereoisomeric forms of general formula (V):

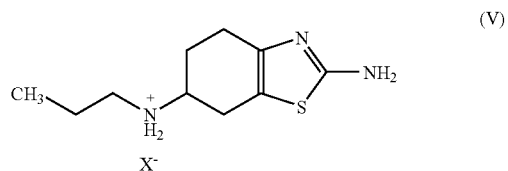

wherein X is the anion corresponding to the salt of the chiral acid of formula (IV).

Another object of the present invention relates to the diastereoisomeric salts of formula (V), constituting the intermediate compounds useful for carrying out the process described in the present invention. In a preferred embodiment, said mono-salts are (R)-2-amino-6-propylamino-4,5,6,7-tetrahydrobenzothiazole(+)-di-p-toluyl-D-tartrate, (S)-2-amino-6-propylamino-4,5,6,7-tetrahydrobenzothiazole(+)-di-p-toluyl-D-tartrate, (R)-2-amino-6-propylamino-4,5,6,7-tetrahydrobenzothiazole(−)-di-p-toluyl-L-tartrate and (S)-2-amino-6-propylamino-4,5,6,7-tetrahydrobenzothiazole(−)-di-p-toluyl-L-tartrate.

DETAILED DESCRIPTION OF THE INVENTION

The present invention describes a new, effective and simple process for the resolution into one of the enantiomers of the racemate of the compound 2-amino-6-propylamino-4,5,6,7-tetrahydrobenzothiazole or for the enrichment of a mixture with any enantiomeric excess of said compound by means of fractionated crystallization of new intermediates corresponding to pure diastereoisomeric salts, or salts enriched in one of their two possible diastereoisomers.

The racemic compound base used as the starting material for the resolution proposed in this document can be obtained by a process such as that disclosed by Spanish patent application P200401559, having the following synthesis scheme:

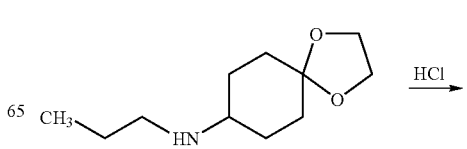

-continued

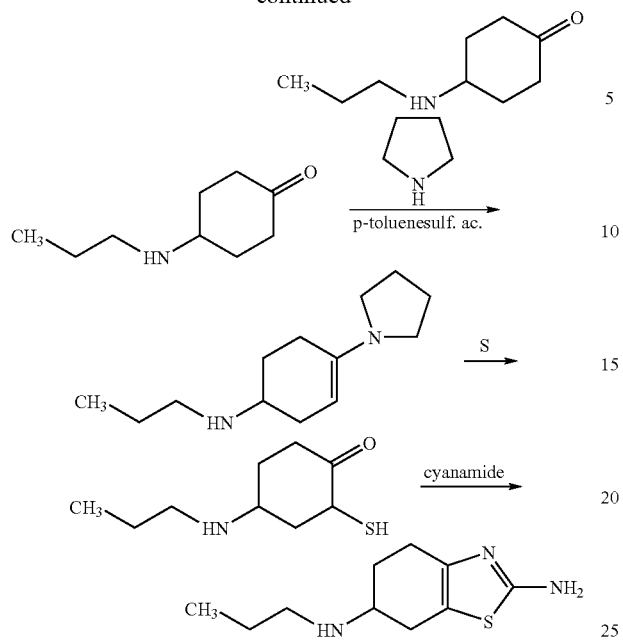

The resolution of 2-amino-6-propylamino-4,5,6,7-tetrahydrobenzothiazole of formula (I):

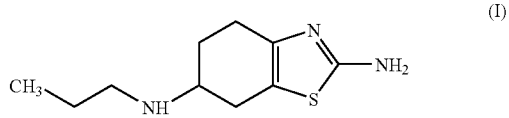

is carried out by means of reacting the racemate or any mixture of enantiomers of compound (I) with optically pure chiral acids of general formula (IV):

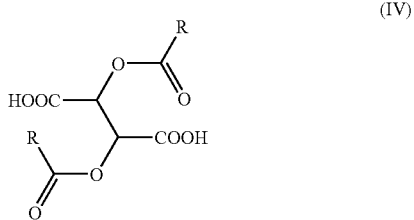

wherein R is monosubstituted phenyl or alkylphenyl, in an organic solvent or in a mixture of said organic solvent and water. Thus, obtained are salts of formula (V):

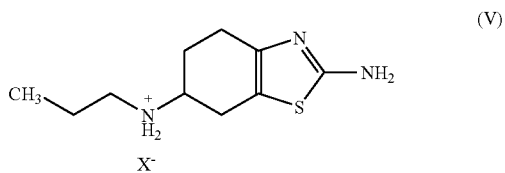

wherein X is the anion of the salt of the chiral acid of formula (IV) which, by means of fractionated crystallization, is split into its pure diastereoisomeric salts or salts enriched in one of the two possible diastereoisomers.

In a preferred embodiment of the invention, the optically pure chiral acids are the two possible enantiomers of di-p-toluyl-tartaric acid of formula:

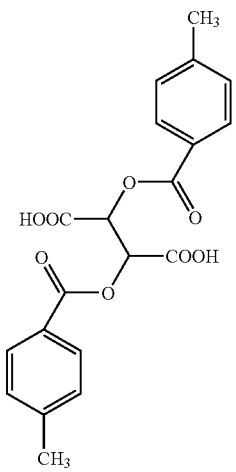

that is, (+)-di-p-toluyl-D-tartaric acid and (−)-di-p-toluyl-L-tartaric acid.

The formation of the diastereoisomeric salts from racemic mixtures of the compound of formula (I) with any of the enantiomers of di-p-toluyl-tartaric acid has different results in reference to the obtained optical purity, depending on the solvent which is chosen. Polar aprotic solvents or alcohols may be used as organic solvents. Nevertheless, it has been observed that when mixtures of conventional organic solvents (alcohols, acetone, acetonitrile) with water are tested, the results improve.

A particular embodiment of the present invention is the use of polar aprotic solvent and water mixtures, preferably the dimethylformamide/water mixture, as the medium for the resolution or enrichment of the diastereoisomeric salts hereinbefore described.

The dimethylformamide/water mixtures provide selectivity when isolating any of the possible salts, high enantiomeric purity, reproducibility and high yields. Particularly, in a resolution and subsequent purification, salts are obtained that are pure enough to obtain pramipexole dihydrochloride with an optical purity making it suitable for marketing. Another one of the advantages found in the use of dimethylformamide/water as a crystallization medium for these salts consists in that any of the possible diastereoisomers can be isolated using only a chiral acid, depending on the dimethylformamide/water ratio.

Therefore in a variant of the process, if (+)-di-p-toluyl-D-tartaric acid and a racemic mixture of the compound (I), or a mixture with any enantiomeric excess, and dimethylformamide/water mixtures in which the water content is less than 5% v/v, are used, mostly the di-p-toluyl-D-tartrate diastereoisomeric salt (+,+) of the (R)-I compound is obtained. In another variant of the process, if (+)-di-p-toluyl-D-tartaric acid and a racemic mixture of the compound (I), or a mixture with any enantiomeric excess, and dimethylformamide/water mixtures in which the water content is greater than 5% v/v and less than 40% v/v are used, mostly the di-p-toluyl-D-tartrate diastereoisomeric salt (−,+) of the (S)-I compound is obtained. In another variant of the process, if (−)-di-p-toluyl-L-tartaric acid and a racemic mixture of the compound (I), or a mixture with any enantiomeric excess and dimethylformamide/water mixtures in which the water content is less than 20% are used, mostly the di-p-toluyl-L-tartrate diastereoisomeric salt (+,−) of the (R)-I compound is obtained. In another variant of the process, if (−)-di-p-toluyl-L-tartaric acid and a racemic mixture of the compound (I), or a mixture with any enantiomeric excess, and dimethylformamide/water mixtures in which the water content is greater than 40% and less than 55% are used, mostly the di-p-toluyl-L-tartrate diastereoisomeric salt (−,−) of the (S)-I compound is obtained.

Depending on the choice of the di-p-toluyl-tartaric acid enantiomer and the dimethylformamide/water mixture, one of the two possible diastereoisomeric mono-salts would mostly be split in a first crystallization, the other diastereoisomeric salt remaining dissolved in the mother liquor, which could be isolated with an even higher purity. Therefore, another aspect of the invention refers to an additional isolation step of the other optically pure diastereoisomeric mono-salt or of a mono-salt enriched in the other diastereoisomeric form of general formula (V):

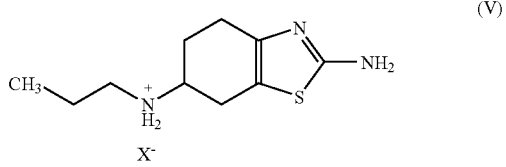

(V)

wherein X is as hereinbefore defined. This additional isolation step of the other mono-salt comprises the addition of water to the mother liquor generated upon isolating the first mono-salt so as to cause precipitation of the said other mono-salt.

The salts obtained in any of the cases described above can be purified for the purpose of increasing their optical purity by simple resuspension or recrystallization in a suitably chosen mixture of dimethylformamide/water.

A second aspect of the present invention refers to the diastereoisomerically pure salts or those enriched in one of the two possible diastereoisomers of formula (V):

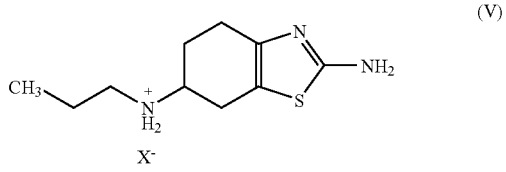

(V)

wherein X is as hereinbefore described.

In a preferred aspect, said salts are (R)-2-amino-6-propylamino-4,5,6,7-tetrahydrobenzoimidazol(+)-di-p-toluyl-D-tartrate, (S)-2-amino-6-propylamino-4,5,6,7-tetrahydrobenzoimidazol(+)-di-p-toluyl-D-tartrate, (R)-2-amino-6-propylamino-4,5,6,7-tetrahydrobenzothiazole(−)-di-p-toluyl-L-tartrate and (S)-2-amino-6-propylamino-4,5,6,7-tetrahydrobenzothiazole(−)-di-p-toluyl-L-tartrate.

Once the desired salt with the suitable optical purity is obtained, it is converted into the corresponding enantiomer of the dihydrochloride compound (I) with the commercially required rotatory power by means of treatment with dichloromethane and a sodium carbonate solution. The rotatory power of the base resulting from evaporating the organic solvent after the corresponding drying is measured in a solution of 10 mg/mL in methanol (c=1.0 methanol).

The previously described process allows resolving the racemic mixture of the compound of formula (I) by obtaining any of the two enantiomers without needing to isolate intermediate mono-salts. The yields and optical purity of the obtained products, the simplicity of the operations and the reproducibility of the process make it applicable from the industrial point of view.

The following examples are provided only as an additional illustration of the invention and must not be taken as a definition of the limits thereof.

EXAMPLES

Synthesis Examples

Example 1

Synthesis of N,N-4-oxocyclohexyl-n-propyl-amine

10% HCl (78 mL) is added to a solution of 4-n-propylaminocyclohexanone ethylene ketal (157 g, 0.85 mol) in water (470 mL). The solution is heated at 95° C.-100° C. in an inert atmosphere for 3 hours. Once the reaction has concluded, the pH is adjusted to 13-14 with 50% NaOH and the aqueous phase is extracted several times with $CH_2Cl_2$. The extracts are washed with a saturated aqueous solution of NaCl and the solvent is removed under vacuum. 84 g (99%) are obtained.

NMR $^1$H (CDCl$_3$): 0.85 (t, 3H), 1.44 (sx, 2H), 1.53-1.64 (m, 2H), 1.98-2.70 (m, 2H), 2.18-2.28 (m, 2H), 2.36-2.44 (m, 2H), 2.50-2.56 (dd, 2H), 2.84-2.90 (m, 1H) ppm.

NMR $^{13}$C (CDCl$_3$): 12.02 (CH$_3$), 23.64, 32.28 (2C), 38.81 (2C), 49.64, 54.09 (CH), 211.83 (C=O) ppm.

Example 2

Synthesis of Base Pramipexole

Pyrrolidine (300 g, 355 mL, 4.25 mol) and p-toluenesulfonic acid.H$_2$O (3.23 g, 0.017 mol) are added to a solution of N,N-4-oxocyclohexyl-n-propyl-amine (133 g, 0.86 mol) in diisopropyl ether (2.7 L). The reaction mixture is stirred at 40° C. for 2 hours. Anhydrous MgSO$_4$ (400 g) is then added and stirred for another 10 hours.

Once this time has elapsed, the suspension is filtered and the solid is washed with diisopropyl ether (200 mL). The solvent is removed under reduced pressure. MeOH (270 mL) is added once the solvent has been removed. Sulfur (32.9 g, 1.2 mol), is added to the solution, stirring for 1 hour. Once this time has elapsed, the mixture is cooled at 0° C.-5° C. and a solution of cyanamide (36.5 g, 0.87 mol) in MeOH (180 mL) is added thereto. The reaction mixture is kept at 0° C.-5° C. for 3 hours and once this time has elapsed, it is allowed to reach room temperature (20° C.-22° C.), maintaining these conditions for another 10 hours.

The reaction mixture is cooled at 0° C.-5° C. and stirred under these conditions for 2 hours. The resulting suspension is filtered, giving 139 g (77%) of base pramipexole with a 98.5% purity (HPLC).

Resolution Examples

Example 3a

Obtaining (S)-pramipexole(+)-di-p-toluyl-D-tartrate (Methanol/Water)

A solution of 3.0 g (14.18 mmol) of (R,S)-2-amino-6-propylamino-4,5,6,7-tetrahydrobenzothiazole (racemic base pramipexole) dissolved in 15 mL of a mixture of a methanol/water (8/2) mixture is added to a solution of 5.48 g (14.18 mmol) of (+)-di-p-toluyl-D-tartaric acid in 75 mL of a methanol/water (8/2) mixture heated at 55-60° C., maintaining the temperature range. The mixture is cooled at room temperature and the suspension is maintained for at least 60 minutes under stirring. The crystals formed by filtration are separated and washed with a methanol/water (8/2) mixture. The resulting solid is dried to constant weight and once dried, 4.0 g of (S)-pramipexole di-p-toluyl-tartrate are obtained (47.1% yield)

NMR $^1$H (DMSO): 0.87 (t, 3H), 1.6 (m, 2H), 2.2 (s, 6H), 2.7 (t, 2H), 5.6 (s, 2H), 6.9 (bs, 2H), 7.4 (d, 2H), 7.9 (d, 2H).

Example 3b

Release of (S)-pramipexole Base 2.0 g (3.34 mmol) of (S)-pramipexole(+)-di-p-toluyl-D-tartrate are stirred in 40 mL of a 7.5% $Na_2CO_3$ w/v solution and 60 mL of dichloromethane until completely dissolved. They are decanted and the phases are separated; the lower organic phase is washed with 10 mL of water. The resulting organic phase after the corresponding decanting is dried with $Na_2SO_4$, filtered and concentrated under vacuum to a residue. The resulting residue is vacuum dried at 40° C. to constant weight. 0.42 g (2.0 mmol, 59.9% yield) of (S)-pramipexole base with a rotatory power of $\alpha_D=-43.0°$ (c=1.0 methanol) are obtained.

Example 4

Obtaining (R)-pramipexole(+)-di-p-toluyl-D-tartrate (97.5 DMF/2.5 Water)

9.14 g (23.66 mmol) of (+)-di-p-toluyl-D-tartaric acid are dissolved in 200 mL of dimethylformamide/water (97.5/2.5) and the solution is heated at 45-50° C. Then, 5 g (23.66 mmol) of (R,S)-2-amino-6-propylamino-4,5,6,7-tetrahydrobenzothiazole (racemic pramipexole base) are added and stirred until dissolved. The mixture is cooled at room temperature and stirred under these conditions overnight. The obtained crystals are filtered and washed with a dimethylformamide/water (97.5/2.5) mixture. The product is dried to constant weight and 5.15 g (8.61 mmol, 36.4% yield) are obtained. The pramipexole base is released as indicated in Example 3b and the rotatory power is measured, being $\alpha_D=76.6°$ (c=1.0 methanol).

Example 5

Obtaining (R)-pramipexole(+)-di-p-toluyl-D-tartrate 5.15 g (8.61 mmol) of (R)-pramipexole di-p-toluyl-D-tartrate($\alpha_D=76.6$, c=1.0 methanol for the released base) are recrystallized in 50 mL of dimethylformamide/water (98/2). Once dried, 3.86 g of the title compound are obtained. The rotatory power for the free base is $\alpha_D=89.9°$ (c=1.0 methanol).

Melting point: 175.2-176.3° C.
NMR $^1$H (DMSO): 0.87 (t, 3H), 1.6 (m, 2H), 2.2 (s, 6H), 2.7 (t, 2H), 5.6 (s, 2H), 6.9 (bs, 2H), 7.4 (d, 2H), 7.9 (d, 2H).

Example 6

Obtaining (S)-pramipexole(+)-di-p-toluyl-D-tartrate (92.5 DMF/7.5 Water)

9.14 g (23.66 mmol) of (+)-di-p-toluyl-D-tartaric acid are dissolved in 200 mL of dimethylformamide/water (92.5/7.5) and the solution is heated at 45-50° C. Then, 5 g (23.66 mmol) of (R,S)-2-amino-6-propylamino-4,5,6,7-tetrahydrobenzothiazole (racemic pramipexole base) are added and stirred until dissolution. The mixture is cooled at room temperature and stirred under these conditions overnight. The obtained crystals are filtered and washed with a dimethylformamide/water (97.5/2.5) mixture. The product is dried to constant weight and 5.37 g (8.98 mmol, 37.94% yield) are obtained. The pramipexole base is released as indicated in Example 3b and the rotatory power is measured, being $\alpha_D=-65.5°$ (c=1.0 methanol).

Example 7

Obtaining (R)-pramipexole(+)-di-p-toluyl-D-tartrate 19.14 g (23.66 mmol) of (+)-di-p-toluyl-D-tartaric acid are dissolved in 200 mL of dimethylformamide/water (98/2) at room temperature. Then, 5 g (23.66 mmol) of (R,S)-2-amino-6-propylamino-4,5,6,7-tetrahydrobenzothiazole (racemic pramipexole base) are added and stirred until dissolution. The mixture is stirred at room temperature overnight and the obtained crystals are filtered, being washed with a dimethylformamide/water (97.5/2.5) mixture. The product is dried to constant weight and 5.38 g (9.00 mmol, 47.0% yield) are obtained. The pramipexole base is released as indicated in Example 3 and the rotatory power is measured, being $\alpha_D=66.7°$ (c=1.0 methanol).

Example 8

Obtaining (S)-pramipexole(+)-di-p-toluyl-D-tartrate 15.6 mL of water are added to the mother liquor resulting from the filtration of the previous example and stirred at room temperature overnight. The obtained crystals are filtered and washed with a dimethylformamide/water (9/1) mixture. The product is dried to constant weight, giving 5.1 g (8.53 mmol, 36.1% yield) of the title compound which, once the base is released as in the prior cases, has a rotatory power of $\alpha_D=-82.6°$ (c=1.0 methanol).

Example 9

Obtaining (S)-pramipexole(+)-di-p-toluyl-D-tartrate 5.1 g (8.53 mmol) of (S)-pramipexole(+)-di-p-toluyl-D-tartrate ($\alpha_D=-82.6°$, c=1.0 methanol for the base released) are recrystallized in 51 mL of dimethylformamide/water (92.5/7.5). Once dried, 4.40 g of the title compound are obtained. The rotatory power for the free base is $\alpha_D=-90.6$ (c=1.0 methanol).

Melting point: 175.2-176.3° C.
NMR $^1$H (DMSO): 0.87 (t, 3H), 1.6 (m, 2H), 2.2 (s, 6H), 2.7 (t, 2H), 5.6 (s, 2H), 6.9 (bs, 2H), 7.4 (d, 2H), 7.9 (d, 2H).

Example 10

Obtaining (R)-pramipexole(−)-di-p-toluyl-L-tartrate 9.14 g (23.66 mmol) of (−)-di-p-toluyl-L-tartaric acid are dissolved in 200 mL of dimethylformamide/water (95/5) at room temperature. Then, 5 g (23.66 mmol) of (R,S)-2-amino-6-propylamino-4,5,6,7-tetrahydrobenzothiazole (racemic pramipexole base) are added and stirred until dissolution. The mixture is stirred at room temperature overnight and the obtained crystals are filtered, being washed with a dimethylformamide/water (95/5) mixture. The product is dried to constant weight and 6.12 g (10.3 mmol, 43.2% yield) are obtained. The pramipexole base is released as indicated in Example 3 and the rotatory power is determined, being $\alpha_D=74.6°$ (c=1.0 methanol).

The resulting solid is recrystallized in 60 mL of a DMF/water (95/5) mixture, the title compound being obtained with a rotatory power value for the base of $\alpha_D=89.8°$ (c=1.0 methanol).

Melting point: 164.6-166.3° C.
NMR $^1$H (DMSO) 0.87 (t, 3H), 1.6 (m, 2H), 2.2 (s, 6H), 2.7 (t, 2H), 5.6 (s, 2H), 6.9 (bs, 2H), 7.4 (d, 2H), 7.9 (d, 2H).

Example 11

(S)-Pramipexole(−)-di-p-toluyl-L-tartrate 36.0 mL of water are added to the mother liquor resulting from the filtration of the previous example (Example 10) and stirred at room temperature overnight. The obtained crystals are filtered and washed with a dimethylformamide/water (75/25) mixture. 9.55 g wet weight of the crude compound are obtained, which are resuspended twice in 50 mL of a DMF/water (75/25) mixture. The crystals obtained by filtration are vacuum-dried to constant weight. 5.2 g (8.7 mmol, 36.7% yield) of the title compound are obtained which, once the base is released as in the prior cases, has a rotatory power of $\alpha_D=-91.0°$ (c=1.0 methanol).

Melting point: 177.3-179.2° C.
NMR $^1$H (DMSO) 0.87 (t, 3H), 1.6 (m, 2H), 2.2 (s, 6H), 2.7 (t, 2H), 5.6 (s, 2H), 6.9 (bs, 2H), 7.4 (d, 2H), 7.9 (d, 2H)

Synthesis Example

Example 12

Synthesis of (S)-2-amino-6-propylamino-4,5,6,7-tetrahydrobenzothiazole dihydrochloride. Pramipexole dihydrochloride 4.40 g (7.36 mmol) of (S)-pramipexole(+)-di-p-toluyl-D-tartrate are dissolved in 88 mL of a 7.5% $Na_2CO_3$ solution and 132 mL of dichloromethane; the phases are decanted and the lower organic phase is washed with 22 mL of deionized water. The phases are decanted and the resulting organic phase is dried with $Na_2SO_4$, filtered and concentrated under vacuum to a residue. The resulting residue is dissolved in 22 mL of methanol and bubbled on the HCl (gas) solution until the pH thereof is comprised between 2.5 and 3.8. It is vacuum-distilled to an internal volume of 12 mL and the suspension is stirred at 0° C. The crystals are filtered, washed with methanol and oven-dried to constant weight. 1.32 g (4.64 mmol, 63.1% yield) of the title compound are obtained. $\alpha_D=-66.5°$ (c=1.0 methanol).

Melting point: 274-284° C.

The invention claimed is:
1. A process for the resolution into one of the enantiomers of the racemate of the compound of formula (I)

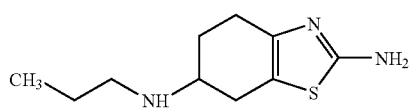

or for the enrichment of a mixture with any enantiomeric excess of said compound of formula (I), comprising the following steps:
a) reacting said racemate, or said mixture with any enantiomeric excess of the compound of formula (I), with any of the enantiomers of a chiral acid of formula (IV):

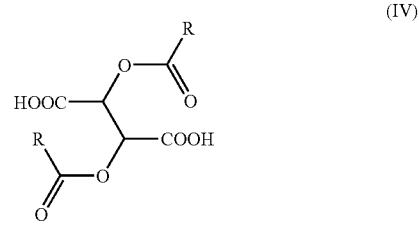

wherein R is monosubstituted phenyl or alkylphenyl, in a polar aprotic solvent and water mixture where said solvent is dimethylformamide; and
b) obtaining, by means of crystallization or fractionated crystallization of the reaction mixture of step a), an optically pure diastereoisomeric mono-salt of general formula (V) or a mono-salt enriched in any of its two possible diastereoisomeric forms of general formula (V):

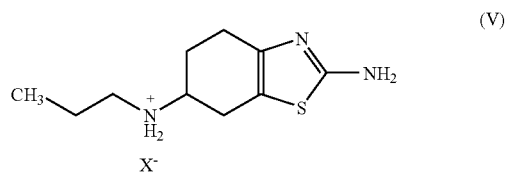

wherein X is the anion of the salt of the chiral acid of formula (IV).
2. The process according to claim 1, wherein the chiral acid of formula (IV) is (+)-di-p-toluyl-D-tartaric acid.
3. The process according to claim 1, wherein the chiral acid of formula (IV) is (−)-di-p-toluyl-L-tartaric acid.
4. The process according to claim 1, for the isolation of a solid enriched in the (R)-2-amino-6-propylamino-4,5,6,7-tetrahydrobenzothiazole (+)-di-p-toluyl-D-tartrate diastereoisomeric salt (+,+), wherein the compound of formula (IV) is (+)-di-p-toluyl-D-tartaric acid and the solvent and water mixture water content is less than 5% (v/v).
5. The process according to claim 1, for the isolation of a solid enriched in the (S)-2-amino-6-propylamino-4,5,6,7-tetrahydrobenzothiazole (+)-di-p-toluyl-D-tartrate diastereoisomeric salt (−,+), wherein the compound of formula (IV) is (+)-di-p-toluyl-D-tartaric acid and the solvent and water mixture water content is greater than 5% and less than 40% (v/v).
6. The process according to claim 1, for the isolation of a solid enriched in the (R)-2-amino-6-propylamino-4,5,6,7-tetrahydrobenzothiazole (−)-di-p-toluyl-L-tartrate diastereoisomeric salt (+,−), wherein the compound of formula (IV) is (−)-di-p-toluyl-L-tartaric acid and the solvent and water mixture water content is less than 20% (v/v).
7. The process according to claim 1, for the isolation of a solid enriched in the (S)-2-amino-6-propylamino-4,5,6,7-tetrahydrobenzothiazole (−)-di-p-toluyl-L-tartrate diastereoisomeric salt (−,−), wherein the compound of formula (IV) is (−)-di-p-toluyl-L-tartaric acid and the solvent and water mixture water content is greater than 40% and less than 55% (v/v).

8. The process according to claim 1, comprising an additional isolation step of isolating the other optically pure diastereoisomeric mono-salt of general formula (V), or of a mono-salt enriched in the other diastereoisomeric form of general formula (V):

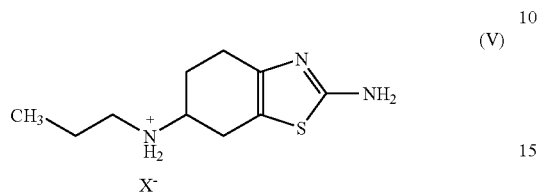

(V)

wherein X is the anion of the salt of the chiral acid of formula (IV).

9. The process according to claim 8, wherein the additional isolation step of the other mono-salt comprises the addition of water to the mother liquor generated upon isolating the first mono-salt of general formula (V), so as to cause precipitation of the said other mono-salt of general formula (V).

* * * * *